(12) United States Patent
Peter et al.

(10) Patent No.: US 8,845,597 B2
(45) Date of Patent: Sep. 30, 2014

(54) ADAPTER FOR AN INJECTION APPLIANCE

(75) Inventors: Daniel Peter, Niederwangen (CH); Reto Sigrist, Golaten (CH); Stefan Jost, Muhleberg (CH)

(73) Assignee: Roche Diagnostics International AG, Rotkreuz (CH)

( * ) Notice: Subject to any disclaimer, the term of this patent is extended or adjusted under 35 U.S.C. 154(b) by 982 days.

(21) Appl. No.: 12/411,858

(22) Filed: Mar. 26, 2009

(65) Prior Publication Data

US 2009/0240211 A1    Sep. 24, 2009

Related U.S. Application Data (63) Continuation of application No. 11/759,640, filed on Jun. 7, 2007, now abandoned, which is a continuation of application No. PCT/EP2005/011856, filed on Nov. 5, 2005.

(30) Foreign Application Priority Data

Dec. 8, 2004  (DE) .................. 10 2004 059 126

(51) Int. Cl.
| | |
|---|---|
| *A61M 5/00* | (2006.01) |
| *A61M 39/12* | (2006.01) |
| *A61M 5/145* | (2006.01) |
| A61M 39/10 | (2006.01) |
| A61M 5/315 | (2006.01) |

(52) U.S. Cl.
CPC ....... *A61M 39/12* (2013.01); *A61M 2039/1033* (2013.01); *A61M 5/31515* (2013.01); *A61M 2039/1077* (2013.01); *A61M 5/14546* (2013.01)

USPC ............ 604/232; 604/152; 604/135; 604/218

(58) Field of Classification Search
USPC ................ 604/152, 232, 234, 235, 240–243, 604/533–536, 538, 135, 218
See application file for complete search history.

(56) References Cited

U.S. PATENT DOCUMENTS

| | | | | |
|---|---|---|---|---|
| 2,526,365 | A | * | 10/1950 | Bjorn ............................ 604/229 |
| 2,646,798 | A | * | 7/1953 | Brown ............................ 604/201 |
| 4,710,179 | A | | 12/1987 | Haber et al. |
| 4,935,014 | A | * | 6/1990 | Haber ............................ 604/195 |
| 5,201,720 | A | * | 4/1993 | Borgia et al. ................. 604/198 |
| 2002/0138046 | A1 | | 9/2002 | Douglas |
| 2002/0173748 | A1 | | 11/2002 | McConnell et al. |
| 2003/0130618 | A1 | | 7/2003 | Gray et al. |
| 2003/0167039 | A1 | | 9/2003 | Moberg |
| 2004/0085215 | A1 | | 5/2004 | Moberg et al. |

FOREIGN PATENT DOCUMENTS

| | | |
|---|---|---|
| DE | 197 40 187 | 4/1999 |
| DE | 600 11 457 | 6/2005 |

* cited by examiner

*Primary Examiner* — Bhishma Mehta
*Assistant Examiner* — Matthew A Engel
(74) *Attorney, Agent, or Firm* — Dinsmore & Shohl LLP (57) ABSTRACT

An adapter for use with an appliance for administering an injectable product, the adapter serving to create a product connection between a catheter and a product container that can be inserted into the appliance, and including a thread for screwing the adapter to the appliance, a stop for fixing the container in the longitudinal direction of the thread, an attachment piece to which the catheter may be connected, and a product channel that extends through the attachment piece and the thread.

13 Claims, 4 Drawing Sheets

FIG. 8

ADAPTER FOR AN INJECTION APPLIANCE

CROSS-REFERENCE TO RELATED APPLICATION(S)

This application is a continuation of U.S. application Ser. No. 11/759,640, filed on Jun. 7, 2007 now abandoned, which is a continuation of International Application No. PCT/EP2005/011856, filed on Nov. 5, 2005, which claims priority to German Application No. 10 2004 059 126.1, filed on Dec. 8, 2004, the contents of which are incorporated in their entirety herein by reference.

BACKGROUND

The present invention relates to devices for delivering, injecting, dispensing, infusing or administering substances, and to methods of making and using such devices. More particularly, it relates to an adapter for an appliance or device for administering an injectable product, such as is used, for example in known injection and infusion appliances and devices, for closing a receiving compartment for a container, generally an ampoule. By such an adapter, the container is fixed in a defined or selected position for dosed administration of a substance therein. In some embodiments, the adapter also creates a product connection between the container, or a container outlet, and a catheter, cannula, needle or the like that is attached to the appliance. The invention further relates to injection and infusion appliances and devices with such an adapter.

In insulin therapy, for example, injection and infusion appliances are used in which a product to be administered is forced from an ampoule, by displacement of a plunger received in the ampoule towards an ampoule outlet, and expelled through a catheter and through an injection needle connected to the latter. The advance, advancing or dispensing movement of the plunger is effected by a drive device. The drive device comprises a manually operated or motor-driven plunger rod which is moved in the advance direction of the plunger. In simple syringes, to which the present invention also relates, such a plunger rod can also be pressed directly by hand in the advancing direction. During its own displacement in the advancing direction, the plunger rod presses the plunger towards the ampoule outlet, as a result of which the product is expelled.

The present invention relates to appliances for product administration in which the plunger received in the container is secured to the plunger rod, by the plunger and the plunger rod being connected, e.g., screwed together, upon insertion of the container.

For this connecting, a person using the known appliances has to grip the container, insert it into the receiving shaft of the appliance and, after obtaining the required contact between the plunger and the plunger rod, screw the plunger onto the plunger rod by turning the container. For reasons of sterility, the container outlet is in most cases closed by a closure cap that has to be removed after the plunger has been screwed on and/or before the receiving compartment is closed. It is also possible for the container outlet to be closed by a membrane, which is pierced by a needle after insertion of the container.

The handling of the container in this procedure is known to be awkward. Moreover, displacements of the plunger in the container until the completion of the screwed connection to the plunger rod are hard to avoid, such that air is sucked into the container or product is expelled at the latest when the closure cap is removed or the membrane pierced.

SUMMARY

An object of the present invention is to make insertion of containers into injection devices and the like safer, easier and more comfortable. The present invention is also intended minimize the chance that the position of the plunger, in the direction of the container axis, is not altered in the container during the connection of the plunger to the plunger rod.

In one embodiment, the present invention relates to an adapter for an appliance for administration, e.g., dosed administration, of an injectable product. The adapter serves to create a product connection between a catheter and a product container, when the container has been inserted into the appliance. The adapter also serves for fixing and/or holding the container in the appliance.

In one embodiment, the present invention comprises an adapter for use with an appliance or device for administering an injectable product, the adapter serving to create a product connection between a catheter and a product container that can be inserted into the appliance, and including a thread for screwing the adapter to the appliance, a stop for fixing the container in the longitudinal direction of the thread, an attachment piece to which the catheter may be connected, and a product channel that extends through the attachment piece and the thread. In one embodiment, an injection device or the like including the adapter is encompassed by the present invention.

In one embodiment, the adapter comprises a thread for screwing the adapter to the appliance, a fixing means for fixing the container in the longitudinal direction of the thread, a catheter attachment piece, and a product channel. A catheter can already be joined to the catheter attachment piece at the time of production. The catheter attachment piece can also be a prepared catheter attachment piece onto which a catheter can be fitted by a user without any further aids, e.g., by screwing the catheter into or onto it. The product channel serves to convey the product from the container into the catheter. It accordingly extends through the adapter. The connection between the adapter and the appliance may be accomplished in any suitable way, including, in some preferred embodiments, by any kind of rotary closure, e.g., a screwed or threaded connection, a bayonet closure, etc.

According to the present invention, the adapter comprises a retaining device by which the container can be connected to the adapter in a manner secured against twisting.

In some embodiments, the container comprises a container wall and a plunger. The anti-twist protection between adapter and container is in this case then an arrangement, feature or structure preventing twisting between the adapter and the container wall. In one embodiment, the plunger is in frictional contact with the container wall and turns along with the container wall, unless it is prevented from doing so by application of external force.

In some preferred embodiments, the retaining device is connected to the adapter in a manner secure against twisting and/or secure against displacement or is likewise connected completely fixedly to the adapter. In principle, however, the retaining device could also conceivably be arranged on or in the adapter loosely, but secure against twisting.

According to some embodiments of the present invention, therefore, the adapter can be used as a container holder when a plunger received in the container is being screwed onto a plunger rod of a drive device of the appliance. A user does not have to directly grip, hold and guide the container during an insertion procedure. For this purpose, he uses the adapter according to the present invention. Since the adapter that creates the product connection can be used as container holder during insertion of the container, a protective cap protecting the container outlet can be removed, and the catheter attached, even before insertion of the container.

In some preferred embodiments, the present invention may comprise a retaining device to hold the container suspended on the adapter. In some illustrative preferred embodiments, the retaining device is formed on an inner jacket of a sleeve part of the adapter that is pushed over the container such that the outlet of the container is guided into the product channel of the adapter, and the outer jacket of the container is held on the adapter in a manner secure against twisting and secure against displacement with the sleeve part of the adapter.

In some preferred embodiments, the adapter and the container are prevented or protected against twisting by a clamping connection, e.g., between a sleeve part of the adapter and the container. A form-fit engagement protecting against twisting is also possible, but it would require a corresponding formation on the outer jacket of the container, for example the formation of protruding cams. By contrast, a clamping engagement secure against twisting is also possible on smooth surfaces. If the container is additionally also held by the retaining device in a manner secure against displacement on the adapter, a clamp-type connection may likewise be used for the connection protecting against displacement.

The combination of the functions of an adapter and of a container holder has an advantage in that, after the container has been inserted and the plunger has been screwed onto the plunger rod, the container holder does not need to be removed again from the container in order to fix the container and create the product connection to a catheter.

In one illustrative embodiment, the thread of the adapter, with which the adapter is screwed onto the administration appliance, has the same pitch as the thread of the plunger rod and of the plunger. In this way, the displacement movements of the adapter and of the plunger, which are associated with the two screwing operations and which take place in the longitudinal direction of the respective thread, are synchronized with one another.

In another illustrative embodiment, the adapter is formed by two adapter parts that are movable relative to one another in the longitudinal direction of the adapter thread. One of the two adapter parts is screwed onto the administration appliance. The other of the two adapter parts forms the retaining device for the container. The two adapter parts are connected to one another in a manner secure against twisting, but are displaceable relative to one another. In some embodiments, the possible displacement movement between the two adapter parts is limited in both directions, e.g., by interacting limit stops formed on both adapter parts. In principle, however, it would also be possible to design the adapter parts such that they can simply be pushed one into the other and removed again from one another. However, handling of the adapter is simplified by the fact that the possible displacement of the two adapter parts is limited at both ends.

DETAILED DESCRIPTION

Figure 1:
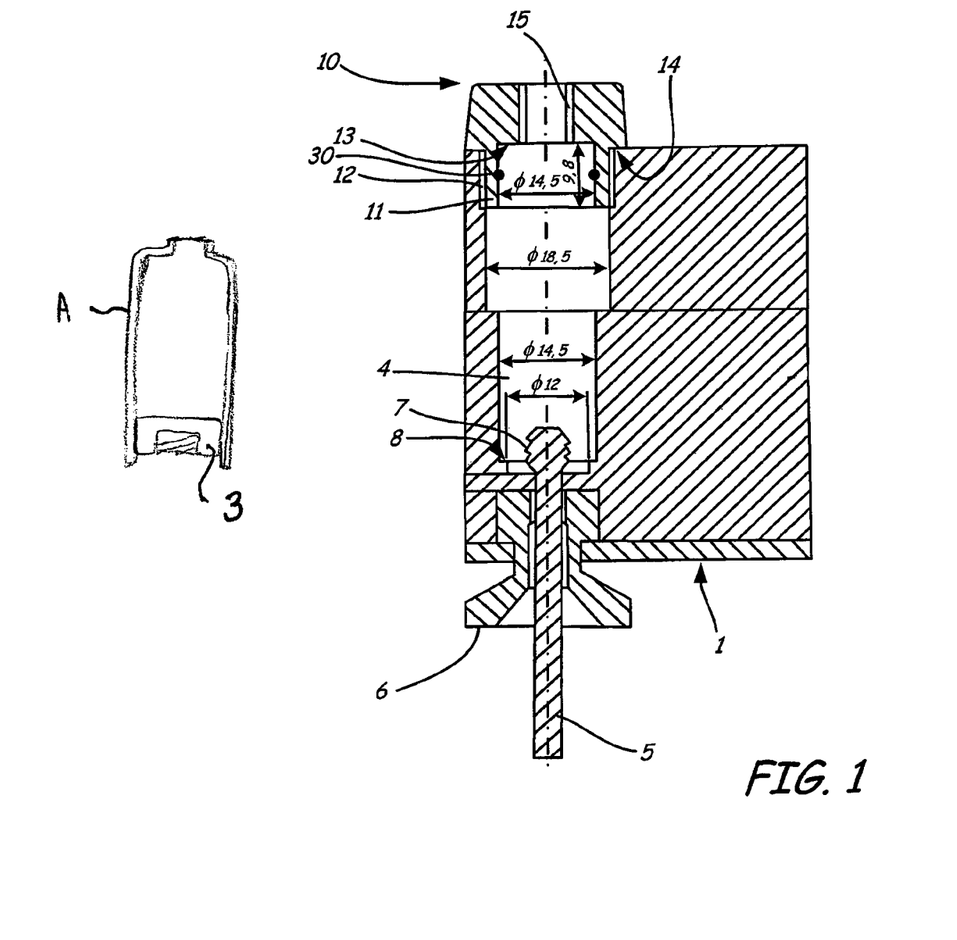
FIG. 1 is a longitudinal section through an administration appliance with an adapter according to one embodiment of the present invention.

FIG. 1 shows an illustrative injection appliance in the form of a manually actuated syringe. A housing 1 of the injection appliance is formed by a housing middle part in combination with a detachable lid connected securely to it and a detachable base plate connected securely to it. In the housing 1, there is a receiving compartment 4 for a container for an injectable product. The receiving compartment 4 is formed as a straight cylinder, in the illustrative embodiment as a circular cylinder, to match the container that is preferably configured as a straight cylindrical ampoule. In FIG. 1, the receiving compartment 4 is shown in its closed state, but without a container. An adapter 10 forms a rotary closure piece for the receiving compartment 4.

In FIG. 1, a product container A is depicted, which is suitable for use with the injection appliance. Container A accommodates a plunger 3 that is guided in a sliding movement therein in a leaktight manner. The plunger closes off the container A towards a rear end of said container A. At a front end of the container A there is an outlet through which product is expelled by displacement of the plunger 3 in an advance direction, i.e. towards the outlet.

The plunger 3 is advanced in the container A by a drive device of the injection appliance. The drive device is formed by a plunger rod 5 and by a drive member 6 for the plunger rod 5. The drive member 6 is a handwheel that is mounted rotatably in the housing 1 but secured against displacement. The plunger rod 5 is guided rectilinearly, and in a manner secured against twisting, in the housing in the advance direction of the plunger 3 when said container A is inserted. The plunger rod 5 and the drive member 6 form a spindle drive in such a way that, by turning the drive member 6, a longitudinal displacement of the plunger rod 5 in or counter to the advancing or dispensing direction of the plunger is obtained.

A head of the plunger rod 5 protrudes into the receiving compartment 4 and is provided with a thread 7. At the rear end of the head of the plunger rod 5, a limit stop flange for the plunger is formed on said plunger rod 5.

The adapter 10 is provided, on a rear sleeve part 11, with an outer thread 12 via which the adapter 10, in the form of the rotary closure piece for the receiving compartment 4, is screwed onto the housing 1. The housing 1, i.e. the lid secured on the housing middle part, which forms a front part of the receiving compartment 4, is for this purpose designed, in the front area of the receiving compartment 4, with an inner thread that matches the outer thread 12.

The adapter 10 is formed by a sleeve body. The sleeve body has a container-retaining part formed by the rear sleeve part 11 and, adjoining this, a front attachment part. The rear sleeve part 11 serves at the same time as a securing part, by means of its outer jacket (it is to be appreciated that, for purposes of the present disclosure, unless clearly indicated otherwise, the term "jacket" may refer to and/or encompass a surface, or other similar structures) being designed with the thread 12 for screwing-in of the adapter 10. The inner cross section of the sleeve part 11 is dimensioned and shaped such that the adapter 10 can be pushed in this area onto a container that can be used with the injection appliance. A clamping means 30 in the form of an O-ring is secured non-displaceably on the inner jacket of the sleeve part 11. In some embodiments, the O-ring is received in a groove extending about the circumference of the inner jacket. The O-ring forms the clamping structure or function 30 for the container and is elastically resilient. A circumferential shoulder protruding inwardly from the inner jacket of the sleeve part 11 forms a front limit stop 13 for the container. A circumferential shoulder protruding outwards from the outer jacket of the adapter 10 forms a limit stop 14 for the adapter 10 when screwed onto the housing 1. The inner and, for the container, front limit stop 13 thus forms a fixing feature, structure and/or method for the container when the container is inserted into the receiving compartment 4 and the adapter 10 is screwed onto the housing 1. In this installation position of the container, said container is fixed in the longitudinal direction, i.e. fixed in and counter to the advance direction of the plunger, by a rear limit stop 8, which is formed by the housing 1, and by the front limit stop 13, which is formed by the adapter 10, or a longitudinal displacement is at least limited.

The attachment part of the adapter 10 is formed by a straight, circular-cylindrical bore and by a sleeve 15 which is pressed into the bore and which is provided, on its inner jacket, with a thread 16 for screwing-in of a tubular catheter. In another embodiment, the sleeve 15 and the thread can also be integrally formed. The bore and the sleeve 15 sitting in it form a prepared attachment means for a catheter.

The adapter 10 facilitates the insertion of a container into the receiving compartment 4. In the insertion procedure, the user first of all removes the protective cap from the Luer cone of the container. The adapter 10 with its sleeve part 11 is then pushed over the Luer cone and then onto the container, until the container abuts the inner limit stop 13 of the adapter 10. In this position, the adapter 10 protects the Luer cone protruding into the bore of the attachment part. At the same time, the clamping force of the elastic clamp 30 ensures that the container is held with clamping on the adapter 10. The clamping engagement is sufficiently strong for the container to be held suspended on the adapter 10. The clamping engagement is also sufficiently strong to avoid twisting of the container relative to the adapter 10 during the subsequent connection of the plunger to the plunger rod 5. In this sense, the adapter 10 forms, with the aid of the clamping means 30, a retaining device for the container.

The catheter is now screwed into the attachment piece 15, and the plunger rod 5 is positioned relative to the plunger in the container.

Upon insertion of the container, the user can push the container, suspended or captured on the adapter 10, into the receiving compartment 4 almost as far as the head of the plunger rod 5. In the course of insertion of the container, the adapter 10 is initially screwed a certain distance into the receiving compartment 4. By the adapter 10 being screwed in, the rear end of the plunger also comes into contact with the head of the plunger rod 5. On the rear end of the plunger there is a blind bore with an inner thread that matches the thread 7 of the plunger rod 5. During the further screwing-in of the adapter 10, and thus the rotation movement of the container obtained by virtue of the retaining device, the plunger is also screwed onto the plunger rod 5 until the plunger abuts the limit stop flange of the plunger rod 5. In some preferred embodiments, this should happen before the container strikes the limit stop 8 or the outer limit stop 14 on the housing 1. If appropriate, the catheter is screwed in more tightly.

Therefore, as the adapter 10 is screwed in further, the underside of the plunger meets a resistance afforded by the limit stop flange of the plunger rod 5. The frictional contact between plunger and container is not sufficient to avoid the plunger turning within the container. By contrast, the anti-twist protection between the adapter and the container wall is maintained during this procedure.

With the adapter 10 in the installed state, the longitudinal axis of the thread 12 of the adapter 10 is aligned with the advance direction of the plunger rod 5. Accordingly, the thread 12 and the plunger thread are also in alignment when the container is held with clamping by the adapter 10, or the longitudinal axes of these two threads can at least be oriented in alignment during the clamping engagement.

The pitch of the thread 12 can be exactly the same as the pitch of the thread 7 or the pitch of the plunger thread. This ensures that the plunger is not displaced, or is displaced only slightly, toward the outlet in the longitudinal direction of the container when the adapter 10, with the container held on it secure against twisting, is screwed onto the housing 1.

If the pitch of the thread 12 is slightly greater than the pitch of the plunger thread, the plunger abuts the limit stop flange of the plunger rod 5 before the container hits the limit stop 8 or the outer limit stop 14 on the housing 1. Slightly greater means, for example, that, over the full length of the thread, the thread 12 has one to three turns fewer than the plunger thread. Nevertheless, the plunger is displaced only slightly towards the outlet in the longitudinal direction of the container.

The feature by which the plunger abuts the limit stop flange of the plunger rod 5 before the container hits the limit stop 8 or the outer limit stop 14 on the housing 1 can also be obtained by the thread length of the connecting thread, between the plunger and the plunger rod 5, being made shorter than the thread length of the adapter 10, given the same thread pitches.

By following the above sequence in the case of the limit stop conditions, it is substantially ensured that there is still some play between the underside of the container and the limit stop 8 when the plunger is already fully screwed to the plunger rod 5. The limit stop 8 can be plastically deformable or can be a spring, such that the container cannot be damaged.

Figure 2:
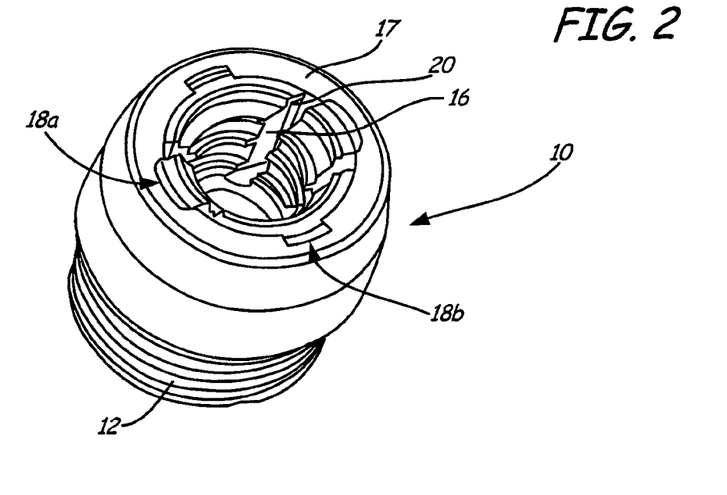
FIG. 2 shows an adapter according to another illustrative embodiment of the present invention.
Figure 3:
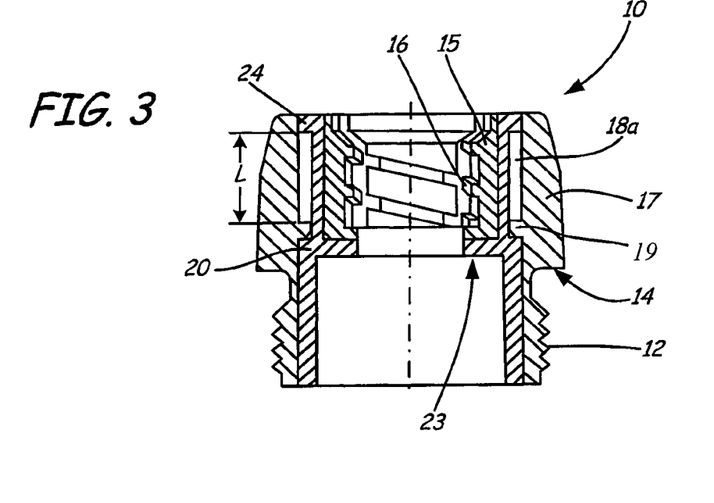
FIG. 3 shows the adapter of FIG. 2 in longitudinal section.

FIG. 2 shows a perspective view of an adapter 10 according to a second illustrative embodiment. In this embodiment of the adapter 10, a securing part 17 of the adapter 10 and a retaining part 20 for the container are able to move relative to one another in the longitudinal direction of the thread 12 of the adapter 10. The function of the adapter 10 according to the second illustrative embodiment can be seen in FIG. 3. The two mutually movable adapter parts, namely the securing part 17 and the retaining part 20, are shown in different individual views in FIGS. 4 to 8, to which reference may additionally be made at the same time.

The securing part 17 is designed as an outer securing sleeve. The retaining part 20 is designed as an inner retaining sleeve in the securing part 17 and can be displaced back and forth along the common longitudinal axis, being guided in a rectilinear manner and secured against twisting. Two longitudinal grooves 18b on an inner jacket of the securing part 17, and two longitudinal webs 29 provided on an outer jacket of the retaining part 20 and engaging in the grooves 18b, serve as rectilinear guides (see FIG. 5). Other rectilinear guides are provided in the form of two further grooves 18a on the inner jacket of the securing part 17 and two hooks 24 which engage in the grooves 18a and which protrude from the outer jacket of the retaining part 20 in a front area of the retaining part 20 and can snap into place.

The two hooks 24 serve as limit stops which limit the relative movement of the retaining part 20 relative to the securing part 17 in a direction which, in the assembled state of the adapter, is counter to the advance direction of the plunger. For this purpose, the grooves 18a are designed as blind grooves which are open to the front edge of the securing part 17 and are delimited, within the securing part 17, by in each case a step which projects inwards from the inner jacket of the securing part 17 and which is formed by a projection 19. At the same time, on a face directed away from the grooves 18a, the projection 19 forms a limit stop shoulder onto which the retaining part 20 abuts with a counter-surface serving as limit stop 26 (see FIG. 4) in the event of a longitudinal displacement in the advance direction of the plunger. In the assembled state of the adapter 10, the end face of the projection 19 directed towards the plunger rod 5 of the injection appliance, for example in FIG. 1, forms, together with the limit stop 26 and with an inner limit stop 23 formed as an inner shoulder of the retaining part 20, the fixing means of the adapter 10 of the second illustrative embodiment.

The securing part 17 is a circular-cylindrical, one-piece sleeve body with a circular-cylindrical inner cross section having two different radii, namely a greater internal diameter in a rear area directed towards the plunger rod 5 in the assembled state, and a by contrast smaller diameter in a front area. The transition between the two areas of different diameters is formed by the projection 19. The two longitudinally continuous grooves 18b and the two blind grooves 18a are formed on the inner jacket of the front area of the securing sleeve 17. The rear area of the securing part 17 is a simple circular cylinder. The outer thread 12 is formed on the outer jacket of the rear area. The outer thread 12 is again delimited by a limit stop shoulder 14 which protrudes radially from the outer jacket of the securing part 17 and which is adjoined by the grip area for the user. The two end faces of the securing part 17 and of the adapter 10 as a whole are simply plane and parallel.

Figure 4:
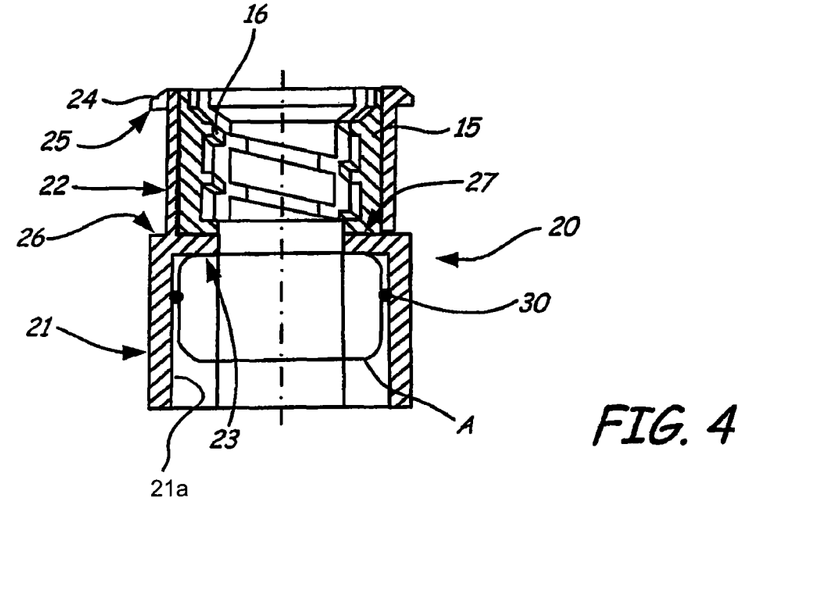
FIG. 4 shows a retaining part of the adapter of FIG. 2 in longitudinal section.
Figure 5:
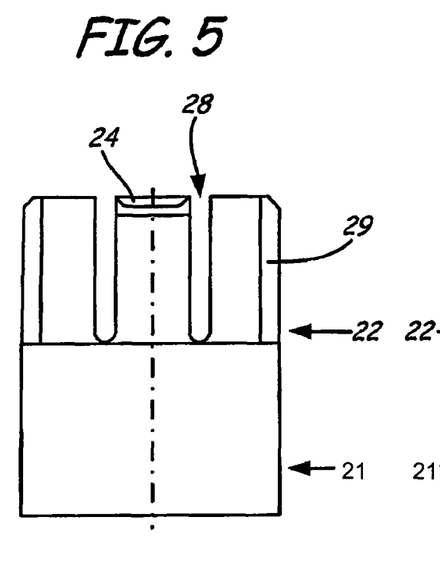
FIG. 5 shows the retaining part of FIG. 4 in one elevation.
Figure 6:
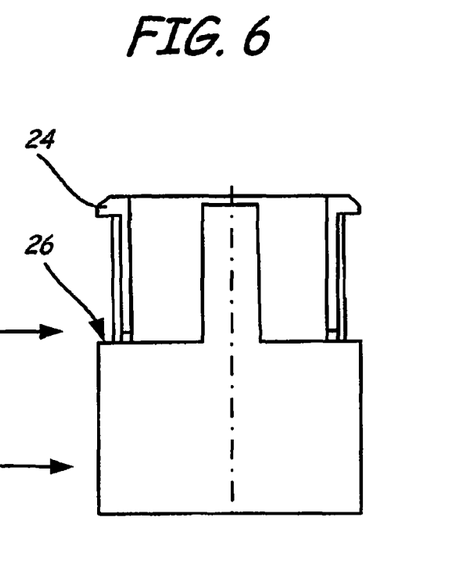
FIG. 6 shows the retaining part in another elevation.
Figure 7:
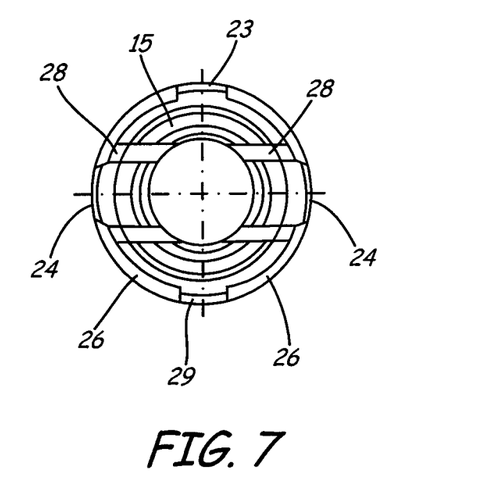
FIG. 7 shows the retaining part in a plan view.
Figure 8:
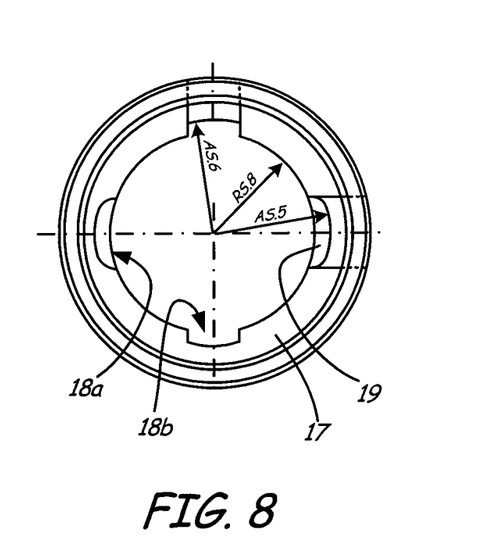
FIG. 8 shows a securing part of the adapter of FIG. 2 in a plan view.

The retaining part 20, depicted in the individual views in FIGS. 4 to 7, is formed by a circular-cylindrical sleeve body with two sleeve areas or sleeve parts 21 and 22. The rear sleeve part 21 is a closed circular cylinder and serves as a receiver and holder for the container, which is indicated in FIG. 4 and is designated by A. For this purpose, a retaining device in the manner of the retaining device of the first illustrative embodiment is formed, by a clamping part 30, in this case an O-ring made of elastomeric material, being arranged on the inner jacket 21a of the rear sleeve part 21, for example being received in a circumferential groove or being otherwise suitably connected non-displaceably (axially) to the retaining part 20. Alternatively, the sleeve part 21 and the clamping part 30 can also be made from two components of plastic. With the aid of the clamping part 30, the container A is clamped on the rear sleeve part 21 in a manner secure against twisting and secure against displacement. In its interior, the rear sleeve part 21 is delimited by the inwardly protruding shoulder 23. With a correct seat inside the retaining part 20, a front edge of the container A abuts against the limit stop 23 thus formed. The sleeve part 21 is adapted to the shape of the containers that can be used with the administration appliance, such that a secure clamping engagement is possible. In the case of circular-cylindrical ampoules, it also has, for example, a circular-cylindrical inner cross section, with a sufficient oversize that is dependent on the thickness and/or elasticity of the clamping part 30.

In its front sleeve part 22, the retaining part 20, in the form of the two longitudinal webs 29 and the two further longitudinal webs with the hooks 24, is slit four times to the height of the limit stop 26. The lengths of the slits are chosen in accordance with the desired flexural elasticity of the hooks 24. In principle, only one of the longitudinal webs 29 and only one of the hooks 24 would be sufficient for this purpose; the two functions could, in principle, also be combined in a single hook with longitudinal guide function. It would also be possible to provide more than two longitudinal webs 29 and/or more than two hooks 24. The two webs with the hooks 24 are set back slightly on their outer jacket to form the two mutually opposed surfaces that serve as limit stops 25 and 26. The two webs with the hooks 24, obtained by the formation of the slits, yield as the retaining part 20 is inserted into the securing part 17, on the projection 19 of the securing part 17. The projection 19 and the hooks 24 have suitably shaped surfaces to promote this yield upon insertion of the retaining part 20. After the hooks 24 have been pushed over the area of the projection 19, the webs with the hooks 24 snap into the groove 18a by virtue of their elastic restoring forces. In this way, the retaining part 20 is hooked in the securing part 17. In the hooked state shown in FIG. 3, the retaining part 20 can be displaced back and forth in the securing part 17 by the displacement length L, in which process the limit stop 25 in the first instance, and the limit stop 26 in the second instance, abuts against the limit stop surfaces formed by the projection 19 of the securing part 17 and in so doing limits the longitudinal displacement. Accidental removal of the retaining part 20 from the securing part 17 is prevented by the shape of the abutting limit stop surfaces of the retaining part 20 and of the securing part 17.

The attachment structure for the catheter is in the form of an attachment sleeve 15 which is pressed into the front sleeve part 22 of the retaining part 20 as far as an inner shoulder 27 of the retaining part 20. Alternatively, the front sleeve part could also be formed integrally on the retaining part 20. The attachment sleeve 15 has an inner thread 16, such that a catheter tube can be screwed into the attachment sleeve 15 and be held securely therein. The attachment sleeve 15 is slit in accordance with the retaining part 20, in the illustrative embodiment four times with corresponding slit lengths, and it is pressed into the retaining part 20 such that the slits of the retaining part 20 and of the attachment sleeve 15 are congruent, as can be seen from FIGS. 2 and 7. If it is suitably resilient, the attachment sleeve 15 can also be produced without slits and can support the hooks 24, which for their part, however, are yielding. Alternatively, the retaining part 20 and the attachment sleeve 15 can also be formed in one piece with one another. Alternatively, the attachment sleeve 15 can also be produced without slits and, after the retaining part 20 has snapped into the adapter 10, can be pressed in such that the hooks 24 are stabilized.

In some preferred embodiments, the securing part 17 and the retaining part 20 are, like the sleeve body of the adapter 10 of the first illustrative embodiment, injection-moulded plastic parts. The attachment sleeve 15 in illustrative embodiments may also be made from a plastic material.

Insertion of a new container A takes place in the same way as with the adapter 10 according to the first illustrative embodiment. An advantage of the adapter 10 according to the second illustrative embodiment is that, because of the longitudinal displaceability of the retaining part 20 relative to the securing part 17, unequal thread pitches of the screwed connections between plunger and plunger rod, on the one hand, and between adapter and housing, on the other hand, may not be required. Moreover, there can also be no relative displacement, or, if any, just a slight relative displacement, of the plunger in the container, for example if the thread 12 of the adapter 10 and the thread 7 of the plunger rod 5 engage in different rotation angle positions of the adapter 10 and of the clamped container A relative to the housing 1. To ensure operating safety, however, the length abutments must provide a limit stop in the discharge direction. In some preferred embodiments, the thread pitch of the plunger/plunger screwed connection is greater than or equal to the thread pitch of the adapter/housing screwed connection.

As shown by the Figures, in some embodiments, the present invention comprises an adapter for an appliance for administering an injectable product, the adapter 10 serving to create a product connection between a catheter and a product container that can be inserted into the appliance, and comprising a thread 12 for screwing the adapter 10 to the appliance, fixing stops or projections for fixing the container in the longitudinal direction of the thread 12, an attachment piece 15 to which the catheter is connected or which is prepared for a connection to the catheter, and a product channel that extends through the attachment piece 15 and the thread 12.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising:
    a housing with a receiving compartment into which a container for an injectable product can be inserted,
    a plunger in the container wherein said plunger can be displaced in an advancing direction toward an outlet of the container,
    a drive device with a plunger rod configured for a threaded connection with the plunger upon insertion of the container into the receiving compartment, and
    an adapter connectable to the housing for fixing the container in the receiving compartment and for forming a product connector between the container and a catheter, the adapter comprising a retaining part by which the container is connected to the adapter such that the container and the adapter cannot be relatively turned, and a securing part with a thread for connecting the adapter to the injection device and one or more longitudinal grooves,
    wherein the adapter is configured such that throughout connection of the adapter to the housing, the retaining part is movable relative to the securing part and guided rectilinearly by the securing part in a longitudinal direction of the screwing-in axis of the thread via the one or more longitudinal grooves, and
    wherein at least one of the one or more longitudinal grooves is open to a front edge of the securing part and is limited by a projection extending radially inward from an inner surface of the securing part.

2. The injection device according to claim 1, wherein the retaining part holds the container suspended on the adapter.

3. The injection device according to claim 1, wherein the retaining part comprises a clamping part made of an elastic material and by which the container is held by a clamping action.

4. The injection device according to claim 1, further comprising a clamping mechanism on an inner jacket of a sleeve part of the adapter, said clamping mechanism pressing elastically against an outer surface of the container.

5. The injection device according to claim 1, the adapter further comprising a stop for securing the container in a longitudinal direction, wherein the stop protrudes inwardly from an inner jacket of a sleeve part of the adapter.

6. The injection device according to claim 1, wherein the retaining part is rectilinearly displaceable relative to the securing part between two limit-stop positions in the direction of the central axis of the thread.

7. The injection device according to claim 1, the adapter further comprising an attachment piece configured for connecting to the catheter, wherein the attachment piece is formed by a sleeve disposed within the adapter.

8. The injection device according to claim 1, wherein the thread of the securing part has a pitch that is smaller than a pitch of a connecting thread between the plunger and the plunger rod.

9. An injection or infusion appliance, comprising:
    a) a housing with a receiving compartment into which a container for an injectable product can be inserted, and a plunger for administering the product is received in the container in such a way that said plunger can be displaced in an advancing direction towards an outlet of the container,
    b) a drive device with a plunger rod onto which the plunger is screwed upon insertion of the container into the receiving compartment, and
    c) an adapter which, to close the receiving compartment, is screwed onto the housing in the longitudinal direction of the plunger rod toward said plunger rod, and which serves for fixing the container in the receiving compartment and as a product connection between the container and a catheter, wherein
    d) the adapter comprises a retaining part by which the container is connected to the adapter in a manner secured against twisting, and a securing part with a thread for connecting the adapter to the injection device, and
    e) the retaining part comprises one or more longitudinal webs extending along a portion of its length and the securing part comprises one or more longitudinal grooves that receive the longitudinal webs such that the retaining part is movable relative to the securing part and guided rectilinearly by the grooves in a longitudinal direction of the screwing-in axis of the thread,
    wherein at least one of the one or more grooves is open to a front edge of the securing part and is limited by a projection extending radially inward from an inner surface of the securing part.

10. The injection appliance according to claim 9, wherein at least one of the one or more webs comprises a hook element on a front end thereof, and wherein the retaining part is rectilinearly displaceable relative to the securing part between a front position and a rear position in which the hook element of the web abuts the projection.

11. An injection device comprising:
    a housing with a receiving compartment into which a container for an injectable product can be inserted;
    a plunger in the container wherein said plunger can be displaced in an advancing direction toward an outlet of the container;
    a drive device with a plunger rod configured for a threaded connection with the plunger upon insertion of the container into the receiving compartment; and
    an adapter connectable to the housing for fixing the container in the receiving compartment and for forming a product connector between the container and a catheter, the adapter comprising
        a securing part formed as a sleeve-shaped member having an open distal end and an open proximal end and a passage extending therebetween, the securing part further having a thread for connecting the adapter to the injection device, and a retaining part, the retaining part being movable within the passage to a position in which a distal end of the retaining part extends substantially to the distal opening of the securing part, the retaining part further having a holding structure configured to hold the container on the adapter such that the container is rotatably fixed relative to the adapter;

wherein the adapter is configured such that throughout connection of the adapter to the housing, the retaining part is movable relative to the securing part and guided rectilinearly by the securing part in a longitudinal direction of the screwing-in axis of the thread, wherein the retaining part further comprises a sleeve part having an open distal end and an open proximal end.

12. The injection device according to claim 11, wherein the sleeve part is coupled to the securing part such that the sleeve part is rotatably fixed relative to the securing part.

13. The injection device according to claim 11, wherein the holding structure is positioned on an inner surface of the sleeve part and is configured to rotatably fix the container relative to the adapter by engaging an outer surface of the container.

* * * * *